(12) United States Patent
Peng

(10) Patent No.: US 6,827,691 B1
(45) Date of Patent: Dec. 7, 2004

(54) OVULATION-PERIOD-DETECTING REAGENTS AND THE USE THEREOF

(76) Inventor: Xiaohong Peng, 60-102, Changxin Apartment, New District, Wuxi City, Jiangsu Province 214028 (CN)

( * ) Notice: Subject to any disclaimer, the term of this patent is extended or adjusted under 35 U.S.C. 154(b) by 0 days.

(21) Appl. No.: 09/644,676

(22) Filed: Aug. 24, 2000

(30) Foreign Application Priority Data

Aug. 25, 1999 (CN) ............................................ 99118909

(51) Int. Cl.⁷ .............................................. A61B 10/00
(52) U.S. Cl. ......................................... 600/551; 422/61
(58) Field of Search .......................... 600/551; 436/164, 436/172, 165, 514; 435/7.21, 7.92, 28; 422/56, 58, 61

(56) References Cited

U.S. PATENT DOCUMENTS

| | | | | |
|---|---|---|---|---|
| 3,406,015 A | * | 10/1968 | Foster | 435/28 |
| 3,472,738 A | * | 10/1969 | Foster | 435/28 |
| 4,614,715 A | * | 9/1986 | Tsibris et al. | 435/28 |
| 5,620,658 A | * | 4/1997 | Jaunakais | 422/61 |

* cited by examiner

*Primary Examiner*—Charles Marmor
(74) *Attorney, Agent, or Firm*—McAndrews, Held & Malloy, Ltd.

(57) ABSTRACT

This invention provides a new reagent for detecting a woman's period of ovulation in a quick convenient manner, comprising Component A which can conduct a color reaction with hydrogen peroxide, and Component B (hydrogen dioxide solution). This invention also provides a kit containing said reagent.

10 Claims, No Drawings

OVULATION-PERIOD-DETECTING REAGENTS AND THE USE THEREOF

FIELD OF THE INVENTION

The present invention relates to a humoral detecting reagent, especially to an ovulation-period-detecting reagent and the use thereof.

BACKGROUND OF THE INVENTION

Nowadays, most fertile women use medical contraception and instrumental contraception. But, most of them suffer a drug by-reaction from medial contraception, and ordinary contraceptive medicines have drawbacks of long period of medicine taking and being liable to be forgotten. Although instrumental conception, such as conception via the loop, has its advantages, the physical malaise to women is also obvious.

In addition to the above-mentioned contraception methods, women usually use the rhythm method, i.e. via calculating their ovulation period. The biggest drawback of this method lies in the fact that the period of ovulation cannot be calculated accurately, and the calculation error would be even bigger if the menstrual cycle is irregular. In this sense, the believed safe rhythm method is not safe.

Since a woman's temperature changes regularly during the period of ovulation, many people predict the period of ovulation by taking the body temperature every day. Obviously, such method is very complicated and tedious.

The inventor has found that before and after the period of ovulation, the content of peroxidase in the vaginal secretion changes remarkably and the peroxidase may catalyze a color reaction between certain substances and hydrogen peroxide. Based on this principle, this invention provides a simple, convenient and reliable method to detect the period of ovulation, thus solving the existing technical problems in the prior art.

SUMMARY OF THE INVENTION

This invention provides an ovulation-period-detecting reagent, comprising:

A first component (e.g. Component A), comprising an aqueous solution of a substance conducting a color reaction with hydrogen peroxide; and A second component (e.g. Component B), an aqueous solution of hydrogen peroxide.

In said Component A, the content of said substance may be 1–10% (by weight), and the content of hydrogen peroxide in Component B may be 1–10% (by weight).

Of the reagent according to this invention, said Component A may further contain a stabilizing agent.

This present invention also provides a kit for detecting the period of ovulation, containing Component A, Component B, a transparent container and cotton sticks. Said Component A comprises 1–10% (by weight) of a substance which can conduct a color reaction with hydrogen peroxide; and said Component B is 1–10% (by weight) aqueous solution of hydrogen dioxide.

This invention is also to provide a method to use said detecting reagent, which comprises mixing said Component A with said Component B, and putting a secretion from the vaginal of the detected woman into the resultant solution, and checking whether or not a color reaction takes place.

DETAILED DESCRIPTION OF THE PREFERRED EMBODIMENTS

According to this invention, the ovulation-detecting reagent comprises a first component (e.g. Component A) and a second component (e.g. Component B), and said Component A further containing a stabilizing agent.

The substance involving in said Component A, which can conduct a color reaction with hydrogen peroxide, is usually selected from benzidine compounds, such as benzidine, tetramethyl benzidine, diaminobenzidine, o-tolidine, o-dianisidine, and the like. Inorganic salts of said benzidine compounds such as hydrochloride and sulfate thereof may also be used as active substances in said Component A.

Besides benzidine compounds, those which can conduct a color reaction with hydrogen peroxide may also be used in this invention. To be specific, said substances include 3-amino-9-ethylcarbazole, 4-methoxy-α-naphthol, o-phenylenediamine, 5-aminosalicylic acid, 2,2-azo-di(3-ethyl-benzothiazoline-6-sulfonate), pyrogallol, o-methoxyphenol, and the like.

Although those stabilizing agents commonly used in this field can be used as the stabilizer in the Component A, sodium benzoate is preferably used in this invention.

This invention further provides a kit for detecting the period of ovulation, which contains a Component A, a Component B, a transparent container and cotton sticks.

In said kit, said Component A and Component B are the same as the above. The content of substances in said Component A (by weight) may be of 1–10%, preferably 5–8%; and the content of hydrogen dioxide in said Component B (by weight) can be of 1–10%, preferably of 4–8%. The proportion between the Component A and the Component B must be kept at a level to satisfy the minimum requirement of the color reaction. Said proportion depends on the specific substance to be used in the Component A, and the appropriate ratio between them (by volume) may be 10–20:1.

In practical use, Component A and Component B are mixed in the transparent container. Then the vaginal secretion collected with a cotton stick is put into the solution to check whether a color reaction takes place, thus determining whether the detected woman is in the period of ovulation.

The principle of this invention is briefly described as follows:

Before and after the period of ovulation, the critical point of peroxidase in the vaginal secretion is usually kept at $25 \times 10^{-3}$–$25 \times 10^{-5}$ u/ml. Within 3–4 days before and after ovulation, the content of peroxidase in the vaginal secretion decreases obviously below the said critical point. Outside the period of ovulation, however, the content of peroxidase in the vaginal secretion is obviously above the critical point. Therefore, it can be determined whether a woman is in the period of ovulation through measuring the content of peroxidase in her vaginal secretion.

The content of said peroxidase is the very content required for catalyzing a color reaction between hydrogen peroxide and certain chemical compounds. Without peroxidase, it would take dozens of minutes or even longer time to finish the color reaction between hydrogen peroxide and the chemical compounds. As a catalyst, however, said content of the peroxidase can make the color reaction finished within a couple of seconds. The present invention is just based on this theory. After the vaginal secretion from a tested woman is put into the mixed solution of Component A and Component B, if the color reaction takes place in the several seconds, it shows that the content of peroxidase in her vaginal secretion is above the critical level. That is, she is in the safe period. Otherwise, she is in the period of ovulation.

The kit for detecting the period of ovulation is specifically used in the following way:

Component A and Component B are mixed in the ratio of 10–20:1 (by volume) and the mixed solution is put into the transparent container. Then, a cotton stick is used to collect some vaginal secretion and the stick is dipped into the prepared reagent. If the color of the reagent does not change, it means that the tested woman is in the period of ovulation. On the contrary, the change of the reagent color indicates that the tested woman in the safe period.

The following clinical experiments have been conducted to test the sensibility and stability of the reagent according to the invention.

1) Experiment of Sensibility:

Test 1:

A 1% solution of sodium benzoate (by weight) was added to a 5% solution of tetramethyl benzidine (hereinafter referred to as: TMB) (by weight) to obtain the Component A, and a 2% aqueous solution of hydrogen peroxide was used to prepare the Component B. Then, three portions of balance samples were made by mixing 1 ml of the Component A with 0.05 ml of the Component B. To the balance samples was added 50 ul of the standard solution with $25 \times 10^3$ u/ml peroxidase, respectively. Other three samples without peroxidase were made as control samples. The result of the experiment was shown in Table 1.

TABLE 1

| Items | Tested Samples | | | Control Samples | | |
|---|---|---|---|---|---|---|
| | 1 | 2 | 3 | 1 | 2 | 3 |
| Component A (TMB) + Component B ($H_2O_2$) | A + B | A + B | A + B | A + B | A + B | A + B |
| Reaction Time (second) | 15 | 15 | 15 | 15 | 15 | 15 |
| Color Displayed | blue | blue | blue | colorless | colorless | colorless |
| Sensibility (%) | 100% | 100% | 100% | 100% | 100% | 100% |

Test 2:

A 1% solution of sodium benzoate (by weight) was added to a 2% solution of 3-amino-9-ethylcarbazole (hereinafter referred to as: AEC) (by weight) to obtain Component A, and a 2% aqueous solution of hydrogen peroxide ($H_2O_2$) was used to make Component B. Then, three portions of balance samples were made by mixing 1 ml of the Component A with 0.05 ml of the Component B. To the balance samples was added 50 ul of the standard solution with $25 \times 10^3$ u/ml peroxidase, respectively. Other three samples without peroxidase were made as control samples. The result of the experiment was shown in Table 1.

TABLE 2

| Items | Tested Samples | | | Control Samples | | |
|---|---|---|---|---|---|---|
| | 1 | 2 | 3 | 1 | 2 | 3 |
| Component A (AEC) + Component B ($H_2O_2$) | A + B | A + B | A + B | A + B | A + B | A + B |
| Reaction Time (second) | 30 | 30 | 30 | 30 | 30 | 30 |
| Color Displayed | red | red | red | yellow* | yellow* | yellow* |

TABLE 2-continued

| Items | Tested Samples | | | Control Samples | | |
|---|---|---|---|---|---|---|
| | 1 | 2 | 3 | 1 | 2 | 3 |
| Sensibility (%) | 100% | 100% | 100% | 100% | 100% | 100% |

*The control sample itself showed yellow color.

The experiment results in Test 1 and Test 2 show that the sensibility reaches 100% within 15–30 seconds.

2) Experiment of Stability:

Tetramethyl benzidine was used to prepare Component A of 5% concentration (by weight). To said Component A was added a 0.01% solution of sodium benzoate as a control sample. The samples were kept still for 6 to 30 months to compare their sensibility. The result was shown in Table 3.

TABLE 3

| Composition of Component A | Valid Time | Sensibility |
|---|---|---|
| TMB | 6 months | 100% |
| TMB | 6–12 months | 50% |
| TMB + Sodium Benzoate | 24–30 months | 100% |

The above result indicates that the stability of the Component A comprising sodium benzoate was increased from 6 months to above 24 months.

3) Clinical Studies:

After two years clinical test of this invention in the hospitals throughout China, the following results have been obtained:

TABLE 4

| Hospitals | Person-times of ovulation period test | Conformity percentage | Person-times of natural contraception | Success percentage |
|---|---|---|---|---|
| Beijing Hospital for Gynecology and Obstetrics | 34 | 100% | 66 | 100% |
| Beijing Hospital | 0 | 0 | 50 | 100% |
| Second Hospital Attached to Nanjing Medical University | 40 | 100% | 10 | 100% |
| Jinan Municipal Hospital for Women and Children | 30 | 94% | 20 | 100% |
| 5th Hospital of Wuxi | 75% | 100% | 25 | 100% |
| 4th Hospital of Wuxi | 35 | 100% | 15 | 100% |
| Total | 241 | 98 8% | 186 | 100% |

The results of clinical experiment showed that 98.8% of the 214 cases of ovulation period test were successful.

In 186 cases of natural contraception, all the target women used the contraception method of the safe period without any other contraceptive measures for 6–24 months in succession and no case of pregnancy occurred, making the success rate of natural contraception 100%.

The invention will be described in detail with the following examples.

EXAMPLE 1

5 kg of tetramethyl benzidine (TMB) was added to 95 kg of medical water, then, 1 kg of 1% solution of sodium benzoate was added to the former solution before being stirred at the speed of 10 rounds/min for 1.0 hour. The stirred solution was kept for 8 hours, and the precipitate was removed to collect the supernatant as Component A in a 20 ml bottle. Hydrogen peroxide and medical water were used to obtain a 1% aqueous solution of hydrogen peroxide as Component B, which was bottled with 2 ml each. Bottles of Component A and Component B together with cotton sticks and a transparent container were packed to obtain a kit of the invention.

EXAMPLE 2

1 kg of the 3-amino-9-ethylcarbazole (AEC) was mixed with 99 kg of medical water to obtain a 1% solution. To the solution was added 1.5 kg of 1.5% solution of sodium benzoate. The resultant solution was stirred at the speed of 12 rounds/min for 0.8 hour and then was kept still for 9 hours. After the precipitate was removed, the supernatant was collected as Component A, which was bottled with 30 ml each. Hydrogen peroxide and medial water were used to prepare a 5% (by weight) solution to obtain Component B, which was bottled with 2 ml each. Bottles of Component A and Component B together with cotton sticks and a transparent container were packed to obtain a kit of the invention.

EXAMPLE 3

10 kg of 4-methoxy-α-naphthol was mixed with 90 kg of medical water to obtain a 10% solution. To the solution was added 2 kg of a 2% solution of sodium benzoate. The resultant solution was stirred at the speed of 15 rounds/min for 0.5 hour and then was kept still for 10 hours. After the precipitate was removed, the supernatant was collected as Component A, which was bottled with 40 ml each. Hydrogen peroxide and medial water were used to prepare a 10% (by weight) solution to obtain Component B, which was bottled with 2 ml each. Bottles of Component A and Component B together with cotton sticks and a transparent container were packed to obtain a kit of the invention.

While the invention has been described in connection with specific embodiments thereof, it will be understood that it is capable of further modifications and this application is intended to cover any variations, uses, or adaptations of the invention, which is defined by the appended claims.

What is claimed is:

1. A kit for determining the period of ovulation of a subject using a secretion from the vagina, comprising: a first component, a second component separately disposed from the first component, a transparent container and cotton sticks, wherein said first component contains 5–8% by weight aqueous solution of a substance which can conduct a color reaction with hydrogen peroxide, said second component is a 4–8% by weight aqueous solution of hydrogen peroxide, and the ratio between said first component and said second component is of 10–20:1 by volume.

2. The kit as claimed in claim 1, wherein said first component further contains a stabilizing agent with a content of 0.01–0.02% by weight.

3. The kit as claimed as in claim 1, wherein said substance in said first component is selected from benzidine compounds.

4. The kit as claimed as in claim 3, wherein said substance in said first component is selected from the group consisting of benzidine, tetramethyl benzidine, diaminobenzidine, o-tolidine, o-dianisidine and an inorganic salts thereof.

5. The kit as claimed as in claim 1, wherein said substance in said first component is selected from the group consisting of 3-amino-9-ethylcarbazole, 4-methyoxy-α-naphthol, o-phenylenediamine, 5-aminosalicylic acid, 2,2-azo-di(3-ethylbenzothiazoline-6-sulfonate), pyrogallol, and o-methoxyphenol.

6. A method for determining whether a subject is in the period of ovulation, comprising the steps of:

mixing a first component with a second component in the ratio of 10–20:1 by volume to obtain a reactive mixture; and placing a secretion collected from the vagina of the subject into the reactive mixture to observe whether or not a color reaction occurs, wherein said first component contains a 5–8% by weight aqueous solution of a substance which can conduct a color reaction with hydrogen peroxide and said second component is a 4–8% by weight aqueous solution of hydrogen peroxide, and the occurrence of the color reaction indicates the subject is not in the period of ovulation.

7. The method as claimed in claim 6, wherein said first component further contains a stabilizing agent with a content of 0.01–0.02% by weight.

8. The method as claimed as in claim 6, wherein said substance in said first component is selected from benzidine compounds.

9. The method as claimed as in claim 8, wherein said substance in said first component is selected from the group consisting of benzidine, tetramethyl benzidine, diaminobenzidine, o-tolidine, o-dianisidine and an inorganic salts thereof.

10. The method as claimed in claim 6, wherein said substance in said first component is selected from the group consisting of 3-amino-9-ethylcarbazole, 4-methyoxy-α-naphthol, o-phenylenediamine, 5-aminosalicylic acid, 2,2-azo-di(3-ethylbenzothiazoline-6-sulfonate), pyrogallol, and o-methoxyphenol.

* * * * *